United States Patent [19]
Geraci et al.

[11] Patent Number: 5,670,308
[45] Date of Patent: Sep. 23, 1997

[54] CRYOPROTECTIVE AQUEOUS SOLUTIONS USEFUL FOR THE PRESERVATION OF IN VITRO CULTURED EPITHELIAL SHEETS

[75] Inventors: Giuseppe Geraci, S. Giorgio a Cremano; Mario De Rosa; Mosé Rossi, both of Naples; Ranieri Cancedda, Genoa; Michele De Luca, Genoa; Graziella Pellegrini, Genoa, all of Italy

[73] Assignees: Development Biotechnological Processes SNC di Pelliccia Maria Teresa, Avellino; Consorzio per la Gestione del Centro di Biotecnologia Avanzata, Genoa, both of Italy

[21] Appl. No.: 446,821

[22] PCT Filed: Dec. 1, 1993

[86] PCT No.: PCT/EP93/03364

§ 371 Date: Jun. 1, 1995

§ 102(e) Date: Jun. 1, 1995

[87] PCT Pub. No.: WO94/13135

PCT Pub. Date: Jun. 23, 1994

[30] Foreign Application Priority Data

Dec. 4, 1992 [IT] Italy .................. MI92A2776

[51] Int. Cl.$^6$ .............. A01N 1/00; C12N 5/00; A61K 35/12
[52] U.S. Cl. .......... 435/1; 435/240.1; 435/240.241; 424/574
[58] Field of Search .......... 435/1, 240.1, 240, 435/241; 424/574

[56] References Cited

U.S. PATENT DOCUMENTS

| | | | |
|---|---|---|---|
| 4,086,218 | 4/1978 | Shanbrom et al. | 260/112 B |
| 4,105,650 | 8/1978 | Shanbrom et al. | 260/112 B |
| 4,439,421 | 3/1984 | Hooper et al. | 424/85 |
| 5,100,676 | 3/1992 | Odessey et al. | 424/574 |
| 5,118,512 | 6/1992 | O'Leary et al. | 424/549 |
| 5,145,770 | 9/1992 | Tubo et al. | 435/1 |
| 5,160,313 | 11/1992 | Carpenter et al. | 600/36 |
| 5,298,417 | 3/1994 | Cancedda et al. | 435/240.1 |

FOREIGN PATENT DOCUMENTS

| | | |
|---|---|---|
| 0296475 | 12/1988 | European Pat. Off. . |
| 0364306 | 4/1990 | European Pat. Off. . |
| 9111101 | 8/1991 | WIPO . |
| 9118505 | 12/1991 | WIPO . |
| 9220300 | 11/1992 | WIPO . |
| 9300807 | 1/1993 | WIPO . |
| 9314191 | 7/1993 | WIPO . |

OTHER PUBLICATIONS

Transplantation, vol. 49, No. 2, Feb. (1990), pp. 261–264, W.N.Wicomb et al. "Optical Cardiopledia and 24–Hour Heart Storage With Simplified UW Solution", etc.

Cryo–Letters, vol. 3, (1982), pp. 115–120, F. Franks, "Apparent Osmotic Activities of Water Soluble Polymers Used as Cryoprotectants".

Breda et al., Cryobiology 29, 281–90 (1992).

*Primary Examiner*—Johann Richter
*Assistant Examiner*—Laura R. Cross
*Attorney, Agent, or Firm*—Griffin, Butler, Whisenhunt & Kurtossy

[57] ABSTRACT

A method for the preservation of in vitro expanded epithelial sheets by incubation of the sheets in a cryopreserving solution characterized by lack of volume increase at the liquid-solid phase transition. The cryopreserving solutions comprise: a) polyethyleneglycols having molecular weight between 3 and 5 KD; and b) at least one cross-linking agent selected from polyols, polyamines, mono- or oligosaccharides, and polyethyleneglycols having molecular weight lower than 1 KD.

6 Claims, No Drawings

CRYOPROTECTIVE AQUEOUS SOLUTIONS USEFUL FOR THE PRESERVATION OF IN VITRO CULTURED EPITHELIAL SHEETS

BACKGROUND OF THE INVENTION

This application is a 371 of PCT/EP93/03364 filed Dec. 1, 1993.

The present invention refers to the preservation, by freezing, of epithelium sheets obtained from cell cultures of keratinocytes.

The cultures of human keratinocytes, developed by. Green and Rheinwald (U.S. Pat. Nos. 4,016,036; 4,304,865; 4,456, 687) raise more and more interest in several medical applications such as in the treatment of serious burns, ulcers, difficult to heal scars and in plastic oncological and reconstructive surgery.

In the case of seriously burnt patients, the death-rate, depending on the patient's age and affected body surface, is dramatically high, particularly for third degree burns greater than 60%. According to the usual procedure, the damaged body surfaces are covered by transplanting skin films removed from healthy areas (auto-grafts); this procedure is very time-consuming and cannot be practically used when the burnt area exceeds 60% of the body surface. The technique by Rheinwald and Green has allowed the burnt areas to be covered with autologous epithelial films obtained from the patient's epithelial cells (keratinocytes). Starting from a small biopsy of epithelial tissue, the technique affords an epithelium surface sufficient to cover the whole body surface in a few weeks.

The autologous transplant in seriously burnt patients represents a unique, socially relevant therapeutic approach.

Autologous transplants are carried out also in cases of plastic oncological and reconstructive surgery. In this case, before surgery, sheets of epithelium expanded in vitro are prepared starting from a patient's biopsy.

The use of cultured human epithelium sheets as "living bandage", for the treatment of ulcers and scars which are difficult to heal, is particularly interesting not only from the social but also from the commercial point of view. In this case, the epidermis sheet, optionally obtained from suitably typized keratinocytes cultures, is used as a temporary dressing of the scar, making the restoring of the epithelium thereon easier thanks to the production of a series of factors stimulating the growth of this tissue, decreasing therefore the patient's suffering and hospitalization.

More than 4 million patients could be treated in the United States with this new therapeutic approach. It is obvious however that this would require remarkably reduced costs of the epithelium sheets, long and easy preservability of the product and easy application procedures in hospital environments.

The method originally developed by Green and Rheinwald for autografts comprises the sampling of a small fragment (2–3 cm$^2$) of epithelium from a healthy area, from which an epithelial cellular suspension is obtained and cultured and finally expanded by means of subsequent passages of the primary cultures. When the secondary and tertiary cultures become confluent, multilayered epithelium sheets are obtained in different sizes according to the need.

Notwithstanding the high potentiality of this therapeutic approach, its wide-scale application is limited by the requirement that the obtained epithelial sheets should be used within a few hours after their preparation.

EP-A-0296475 discloses a method for preserving at −100° C. viable, transplantable epithelium sheets cultured in vitro, frozen in a nutrient medium containing the usual cryopreserving agents such as dimethylsulfoxide or glycerine.

Although this method has allowed for the first time the preservation of in vitro cultured epithelium sheets, a number of problems limit its industrial applicability:

a) the permanence in the preserving medium before freezing is extremely critical for the cells at room temperature. This makes critical the initial step of the preserving process, comprising an incubation at room temperature to equilibrate the epithelium sheets with the solution and the final phase of thawing before using the sheets. In both cases, a few minutes difference in the performance of these steps may (irreparably) impair the characteristics of the product;

b) The complexity of the cooling cycle of the samples, critically characterized by different cooling rates in particular temperature ranges involve expensive industrial apparatuses and high production costs;

c) The preserved product is very sensitive to even slight changes in the preservation temperature, which can cause alteration of the product preventing its use;

d) The shipment of the sample to the utilization sites must necessarily be carried out at a temperature constantly kept at about −80° C. and similar measures must be observed by the hospitals before the use of the product;

e) Cell viability in the frozen graft obtained by this procedure can be, in the best conditions, up to 70%. However given the critical steps required for freezing (see points a, b, c, d) the large variability of the obtained results makes this procedure difficult to use in large scale preparations.

The present invention aims at overcoming the above limitations and allowing the industrial applicability of the production and preservation processes of human epithelium sheets optionally typized, convenient methods of use in hospital environments and costs compatible with the previously cited therapeutic uses.

BRIEF DESCRIPTION OF THE INVENTION

The above problem is solved by the present invention which provides a new kind of cryoprotective solutions which allow the preserving of frozen cultured human epithelial sheets for a long time.

According to the invention, the processing times are not critical both before freezing and in hospitals where thawing and grafting take place.

Moreover, the quality of the graft frozen with the new procedure is much superior in cell viability which can be up to 100% in the best conditions. At variance with grafts frozen with the old procedure the frozen sheets, preserved in these new cryoprotective solutions, do not undergo functional alterations impairing their use, even if the preservation temperature is subjected to changes of tens of degrees or the sample is accidentally thawed for a short period of time.

It is known that in the cryopreservation of biological material in aqueous solutions, the formation of ice crystals, connected with the regular growth of the crystalline reticulum, brings about a high risk of mechanical destruction of cell structures situated along the path of crystal growth. This occurs both outside the cells, in the solutions where they are placed for the freezing phase, and inside the cells themselves. This drawback is only partially overcome by using cryopreserving agents such as glycerine, dimethylsulfoxide etc.

The very high pressures acting on the cell structures when water passes from the liquid to the solid state act synergistically with the mechanical damage deriving from the formation of ice needles. The volume increase for aqueous solutions is up to 10%.

Both the crystal formation and the volume change at the liquid-solid transition phase usually occur in the solutions presently used for the cryopreservation of biological material and are the main cause of the viability loss of the cryopreserved samples. The present invention provides cryopreserving solutions in which the liquid-solid transition phase occurs without volume increase and macrocrystal formation, providing therefore improvements over the prior-art methods and solving in an economic and convenient way the many problems of the cryopreservation of biological material, particularly those previously cited for the preservation of frozen epithelial tissue sheets.

The solutions of the invention comprise:
a) polyethylene glycols (PEG) having molecular weight not higher than 20 KD, preferably from 3 to 5 KD, at concentrations not higher than 25% w/w, preferably from 10 to 20% w/w;
b) at least one low molecular weight compound, defined as a cross-linking agent in view of its ability to form with the polymer and with water cross-linked systems based on hydrogen bends, in concentrations not higher then 25% w/w, preferably from 5 to 20% w/w. The cross-linking agents are selected from polyols (glycerine, ethylene glycols, maltitel, inositol), mono and oligosaccharides (glucose, sucrose, maltodextrins) and PEGs having molecular weight lower than 1 KD. Glycerine is preferably used.

The solutions of the invention may be prepared in physiological saline solutions and may contain antibiotics, proteins, sera and other compounds usually used for the growth and culture of biological materials.

More particularly, solutions suited for the cryopreservation of viable, in vitro grown epithelium sheets are prepared by adding in suitable concentrations PEG and glycerol as cross-linking agent, preferably 13% w/v PEG an 15% w/v glycerol to media optimized for the keratinocytes growth such as 60% v/v Dulbecco modification of Eagle's medium, 30% v/v Ham's F12, 10% v/v Fetal calf serum (FCS), containing glutamine 4 mM, adenine $1.8\times10^{-4}$M, insulin 5 µg/mL, transferrine 5 µg/mL, triiodothyronina $2\times10^{-9}$M hydrocortisone 0.4 µg/mL, penicillin-streptomycine 50 U/mL.

The sheets are first washed in the cryopreserving solution and then introduced into suitable bags containing 100–200 ml of solution.

After closing the containers, the samples are allowed to equilibrate at room temperature for periods not longer than 1 h, preferably from 5 to 10 min.

Freezing of samples may be carried out by simply cooling the containers to the preservation temperature, generally from –25 to –100° C., preferably –80° C.

Thawing of samples may be carried out by dipping the frozen container in a bath at 37° C. for 5–10 min. In order to make this step less critical, especially when not particularly qualified users have to handle such delicate cellular materials, and to minimize stress to which thawed cells may be subjected by the high concentration of cryoprotective agents in the liquid phase, thawing of epithelial sheets may be carried out in a special container consisting of two compartments which are interconnected when the sample is thawed, one containing the epithelial sheets in the cryopreserving solution and the other, containing a nutrient medium or isotonic saline solution. During thawing, the two solutions are mixed, causing the dilution of cryoprotective agents minimizing thereby possible cellular damage.

The human epithelial sheets cryopreserved in the solutions of the invention are equivalent to the fresh ones not subjected to freezing, both as far as the morphology and the after graft are concerned.

The solutions of the invention may also be used for the preservation of cells used for the preparation of the sheets. These comprise, for instance, 3T3 cells to be used as feeder layer or keratinocytes isolated and dissociated from biopsies.

The following examples further illustrate the invention.

EXAMPLE 1

Keratinocytes cultures were obtained according to the method of Rheinwald and Green. The secondary confluent keratinocytes cultures obtained according to U.S. Pat. No. 4,016,036 are detached from culture flasks, transferred on suitable support and anchored by means of metal clips for vascular surgery according to the method of U.S. Pat. No. 4,304,866.

The so prepared sheets are washed by immersion in sterile conditions in 100 ml of the cryopreserving solution consisting of 60% v/v Dulbecco modification of Eagle's medium, 30% v/v Ham's F12, 10% v/v FCS, glutamine 4 mM, adenine $1.8\times10^{-4}$M, insuline 5 µg/mL, transferrine 5 µg/mL, triodothyrosine $2\times10^{-9}$M, hydrocortisone 0.4 µg/mL, epidermal growth factor (EGF) 10 ng/mL, penicilline-streptomicine 50 U/mL, PEG 3350 13% p/v, glycerol 15% p/v.

The sheets are then transferred under sterile conditions in 15×10 cm plastic envelopes, previously sterilized and containing 100 ml of the above reported cryopreserving solution.

The plastic envelopes are then heat sealed and then transferred, without any particular precaution, to the freezer and cooled to a temperature ranging from –25° and –100° C., preferably –80° C. The duration of the operations bringing the epithelial sheets into contact with the cryopreserving solution at room temperature is not critical and may range from a few minutes to 1 h, preferably 5–10 min, without negative consequences in the clinical use of the preserved material.

The liquid-solid transition phase of the solution occurs between –10° and –15° C. and the cooling rate of the samples is not critical and the preserving temperature may vary even by tens of degrees without affecting viability of the preserved material.

The epithelial sheets may be preserved at –80° C. for several months, whereas at higher temperatures this period is slightly shortened. The envelopes containing the frozen epithelial sheets may be shipped in solid $CO_2$ or at higher temperatures up to –20° C. and the therapeutic use is not impaired by temperature changes of tens of degrees or by a short accidental thawing.

Immediately before use, the envelopes, taken out of the freezer are immediately introduced into a water bath at 37° C. for 5–10 min and then immersed for a few seconds in 70% ethanol. After opening in sterile conditions, the epithelial sheets are transferred into sterile containers, thoroughly washed with a medium free from serum and additives or with saline solution before use.

The thawed samples are subjected to the following characterizations:
a) histology of the sheet, morphological exam and evaluation of the keratins typical of the various differentiative degrees;

b) trypsinization and low density plating to evaluate the number and size of the formed colonies;
c) microscopic evaluation of the cellular morphology and of the number of viable cells;
d) biological tests of graftability on derma or other vital receiving bed, such as nude mice.

The overall results of these characterizations show that cryopreserved epithelial sheets in the solutions of the invention remain viable and show characteristics comparable to those of fresh sheets which have been not cryopreserved.

EXAMPLE 2

Epithelial sheets cryopreserved at −80° C. for 30 days, as disclosed in Example 1, are thawed by immersing for 5–7 min the container in a bath at 37° C. and, after opening in sterile conditions, the epithelial sheets are washed in 100 ml of culture medium consisting of 60% v/v Dulbecco modification of Eagle's medium, 30% v/v Ham's F12, 10% v/v FCS, glutamine 4 mM, adenine $1.8\times10^{-4}$M, insuline 5 μg/mL, transferrine 5 μg/mL, triodothyronine $2\times10^{-9}$M, hydrocortisone 0.4 μg/mL, EGF 10 ng/mL, penicillin-streptomycine 50 U/mL.

The sheets are then treated with trypsine and dissociated into single cells which are cultivated on a bed of irradiated fibroblasts, as disclosed in U.S. Pat. No. 4,016,036. When keratinocytes colonies are subconfluent the culture medium is removed, the cell layer is washed with FCS-free culture medium and then treated with trypsine to dissociate colonies into single cells.

The obtained cellular suspension is centrifuged, suspended again in 5 ml of cryoprotective solution, centrifuged again at 1000 g for 5 min, the solution is removed, the cell pellet is suspended in 1.5 ml of cryoprotective solution and frozen to −80° C. in three aliquots. At different time intervals, ranging from week to 3 months the cells are thawed by placing the closed vial for 5–7 min in a bath at 37° C., 5 ml of fresh medium are added, the suspension is centrifuged at 1000 g for 5 min and suspended again in the medium with which the culture on irradiated fibroblasts is started, as reported in U.S. Pat. No. 4,016,036 until a multi-layer epithelium is obtained on which the following characterizations are carried out:
a) histology of the sheet, morphological exam and evaluation of the keratins typical of the various differentiative degrees;
b) trypsinization and low density plating to evaluate the number and size of the formed colonies;
c) microscopic evaluation of the cellular morphology and of the number of viable cells;
d) biological tests of graftability on derma or other vital receiving bed, such as nude mice.

The results of these characterizations show that the cells deriving from epithelium sheets cryopreserved in the solutions of the invention, after enzymatic treatment and freezing, remain perfectly viable and keep their characteristics and differentiative features, as shown by the ability of yielding again epithelial sheets fully comparable to sheets obtained from non frozen cells.

We claim:
1. Cryoprotective aqueous solutions for preservation of in vitro cultured epithelial sheets comprising:
   a) from 10 to 20% w/w of polyethyleneglycols having molecular weight from 3 to 5 KD;
   b) from 5 to 25% w/v of at least one cross-linking agent selected from the group consisting of polyols, polyamines, mono- and oligosaccharides, and polyethyleneglycols
   having a molecular weight lower than 1 KD; and
   wherein a) and b) are in proportions sufficient to provide a cryoprotective aqueous solution for epithelial sheets.

2. Solutions according to claim 1 wherein the cross-linking agent b) is selected from the group consisting of glycerol, maltitol, glucose, fructose, sucrose and maltodextrins.

3. Solutions according to claim 1 also containing one or more of antibiotics, proteins and sera.

4. Solutions according to claim 1 which include an added media comprising 60% v/v Dulbecco modification of Eagle's medium, 30% v/v Ham's F12, and 10% v/v Fetal calf serum (FCS) comprised of glutamine 4 mM, adenine $1.8\times10^{-4}$M, insuline 5 μg/mL, transferrine 5 μg/mL, triiodothyronina $2\times10^{-9}$M, hydrocortisone 0.4 μg/mL, Epidermal Growth Factor (EGF) 10 ng/mL and penicillin-streptomycine 50 U/mL.

5. A method for the cryopreservation of epithelial sheets obtained from keratinocytes cultures comprising:
   a) incubation at room temperature of said epithelial sheets in a cryopreserving solution of claim 1, for a time shorter than 1 h, and
   b) freezing the epithelial sheets in said solution at temperatures from −100° to −25° C.

6. A method for the preservation of cells used for the preparation of epithelial sheets expanded in vitro comprising:
   a) incubation at room temperature of said cells in a cryopreserving solution of claim 1, for a time shorter than 1 h, and
   b) freezing the epithelial sheets in said solution at temperatures from −100° to −25° C.

* * * * *